United States Patent [19]

Rahman et al.

[11] 4,419,348
[45] Dec. 6, 1983

[54] ANTHRACYCLINE GLYCOSIDE COMPOSITIONS, THEIR USE AND PREPARATION

[75] Inventors: Aquilur Rahman, Rockville; Philip S. Schein, Bethesda, both of Md.

[73] Assignee: Georgetown University, Washington, D.C.

[21] Appl. No.: 258,016

[22] Filed: Apr. 27, 1981

[51] Int. Cl.³ .................. A61K 31/70; C07H 17/08
[52] U.S. Cl. ........................... 424/180; 424/177; 424/182; 536/6.4; 536/5
[58] Field of Search .............. 424/180, 182, 177; 536/5, 17 A, 6.4

[56] References Cited

U.S. PATENT DOCUMENTS

| | | | |
|---|---|---|---|
| 3,993,754 | 11/1976 | Rahman et al. | 424/177 |
| 4,256,632 | 3/1981 | Levin et al. | 536/17 A |
| 4,263,428 | 4/1981 | Apple et al. | 536/17 A |

*Primary Examiner*—Johnnie R. Brown
*Attorney, Agent, or Firm*—Oblon, Fisher, Spivak, McClelland & Maier

[57] ABSTRACT

Anthracycline glycoside antibiotics are complexed with cardiolipin and then encapsulated in liposomes to reduce mammalian cardiac tissue uptake of the anthracycline glycoside and to thereby reduce the deleterious effect of such cardiac tissue uptake. The invention is directed to the composition, preparation and use of the encapsulated complex of anthracycline glycoside.

15 Claims, 3 Drawing Figures

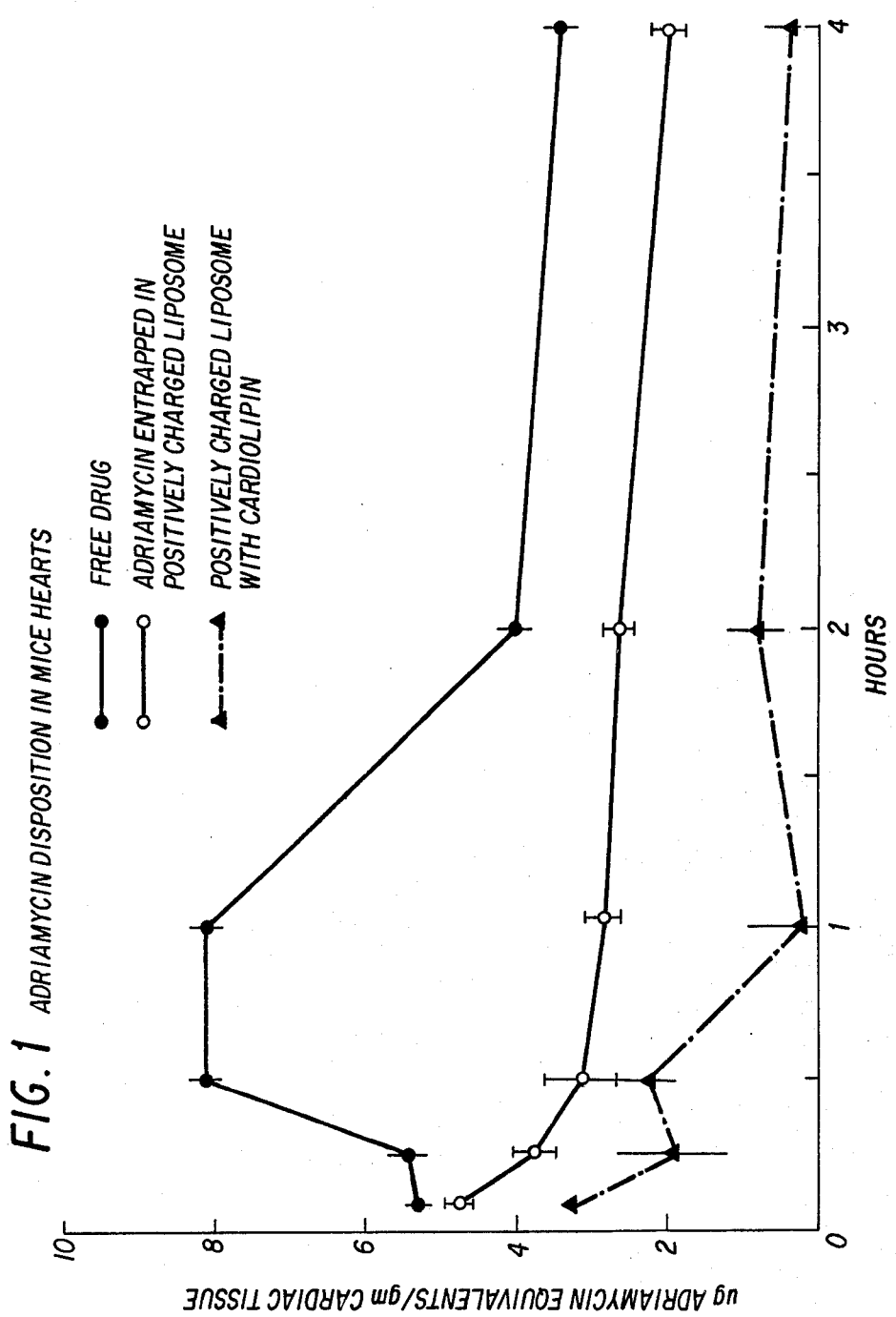

FIG. 2 ELECTRON MICROGRAPH OF CARDIAC TISSUE FROM DBA/2 MOUSE ADMINISTERED 15mg/kg i.v. FREE ADRIAMYCIN SHOWING LOSS AND FRAGMENTATION OF MYOFILAMENTS WITH CONCOMITANT CLEARING OF ORGANELLES AND SWELLING OF SARCOPLASMIC AREAS. NOTE CLEARANCE OF OCCURRENCE ADJACENT TO VASCULATURE. x4000

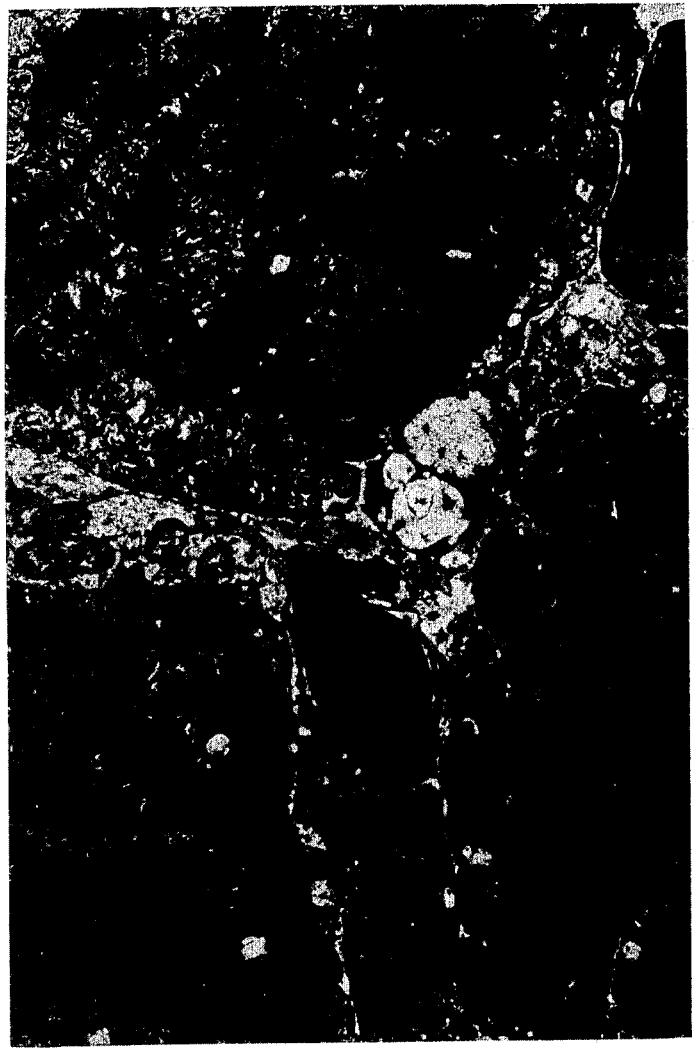
FIG. 3  ELECTRON MICROGRAPH OF CARDIAC TISSUE FROM DBA/2 MOUSE GIVEN 15mg/kg i.v. ADRIAMYCIN ENTRAPPED IN CARDIOLIPIN LIPOSOMES. ESSENTIALLY NORMAL APPEARING MYOCARDIUM. LIMITED TOXIC DAMAGE MANIFESTED AS VACUOLIZATION SEEN IN VASCULAR ASSOCIATED TISSUES BETWEEN ADJACENT MYOCYTES

4,419,348

ANTHRACYCLINE GLYCOSIDE COMPOSITIONS, THEIR USE AND PREPARATION

BACKGROUND OF THE INVENTION

The anthracycline glycosides are antibiotics in which a tetrahydronaphthacene chromophore is linked to a sugar, most commonly a basic sugar. Representative anthracycline glycoside antibiotics include doxorubicin
daunorubicin
daunorubicinol
doxorubicinol and pharmaceutically acceptable analogues, derivatives and salts thereof.

Anthracycline glycosides, such as doxorubicin HCl (Adriamycin, a product of U.S. Pat. No. 3,590,028) and daunorubicin (U.S. Pat. No. 4,012,284) and pharmaceutically acceptable analogues, derivatives and salts thereof, are also known oncolytic agents. Representative analogues are described in U.S. Pat. No. 3,686,136 and K. Yamamoto et al., *J. Med. Chem.* 15, 872 (1973); German Pat. Nos. 2,327,211; 2,557,537; and 1,920,198; E. Bachman et al., *Agents and Actions* 5/4, 383 (1975); P. Chandra, *Cancer Chemother.* Rep. 6, 115 (1975); F. Arcamone et al., id. at 123; and G. Zbinden et al., *Cancer Chemother.* Rep. 4, 707 (1975), the disclosures of which are incorporated herein by reference.

Overall usefulness of the anthracycline glycosides as antibiotics and oncolytic agents is severely restricted because of inherent treatment-limiting and potentially lethal cardiotoxicity. The cardiotoxic effects of doxorubicin HCl (Adriamycin) and daunorubicin have been documented (U.S. Pat. No. 4,138,480). Cumulative myocardial damage has been correlated with Adriamycin doses in excess of 500 mg/m$^2$, or less in patients with prior medastinal irradiation, and takes the form of refractory congestive heart failure. Electron microscopic studies of the heart tissue in such cases have demonstrated a striking degeneration of myofibrills and mitochondrial distortion as well as a decrease in cardiac myocytes, Lefrak, E. A., Pitha, J., Rosenheim, S., O'Bryan, R. M., Burgess, M. A., Gottlieb, J. A.: Adriamycin (NSC-123127) Cardiomyopathy. *Cancer Chemother.* Rep. 6:203-208 (1975). Pharmacokinetic studies have shown that Adriamycin (doxorubicin HCl) is taken up avidly and preferentially by heart muscle, Yesair, D. W., Schwartzbach, E., Shuck, D., Denine, E. P., Asbell, M. A.: Comparative pharmacokinetics of Daunomycin and Adriamycin in several animal species. *Cancer Research* 32:1177-1183 (1972). It is known that administration of Adriamycin (doxorubicin HCl) causes the occurrence of cardiac toxicity at doses lower than recommended cumulative limit and therefore it is not recommended to start the use of doxorubicin HCl in such cases. Also, starting treatment is contraindicated in cases where there has been previous treatment with complete cumulative doses of Adriamycin and/or daunorubicin.

The present invention is directed to a delivery system which will selectively reduce the uptake of anthracycline glycoside drugs, such as doxorubicin HCl, in cardiac tissue, while preserving the drug's antibiotic and antitumor activity.

DESCRIPTION OF THE INVENTION

The invention is directed to a delivery system for a mammalian host based on an anthracycline glycoside composition which exhibits therapeutic benefits but also is characterized by preferential cardiac tissue uptake by the host with attendant cardiotoxicity and cardiomyopathy. The delivery system itself preserves the therapeutic activity of the anthracycline glycoside while selectively reducing the host's cardiac tissue uptake of the composition and thereby substantially reducing the side effects of cardiotoxicity and cardiomyopathy. The delivery system is based on a composition comprising an anthracycline glycoside, cardiolipin and liposomes. The methods of the invention include preparation of and administration of the composition.

The anthracycline glycoside of the composition of the invention may be any which exhibits antibiotic and/or oncolytic activity and is characterized by cardiac tissue uptake in a mammalian host and by attendant cardiotoxicity and/or cardiomyopathy and may be a non-toxic pharmaceutically acceptable analogue, derivative or salt thereof. It is well documented that doxorubicin hydrochloride (Adriamycin) and daunorubicin are such anthracycline glycosides. In a specific embodiment of the invention, the anthracycline glycoside is Adriamycin.

In accordance with the invention, the anthracycline glycoside is complexed with cardiolipin. In the anthracycline glycoside-cardiolipin complex, the cardiolipin is at least physically bonded to the anthracycline glycoside. The amount of cardiolipin in the anthracycline glycoside-cardiolipin complex can range from about 30% to about 70%, based on the weight of the anthracycline glycoside. The anthracycline glycoside-cardiolipin complex is formed by admixing the anthracycline with the cardiolipin in a solvent for a time sufficient to allow complex formation and then isolating the complex by evaporating the solvent. The solvent may be any fluid in which each component is soluble; in a specific embodiment of the invention such a solvent is methanol. Evaporation of the solvent is preferably undertaken by blowing gas into the complex containing solution which is inert with respect to the complex and its components, such as nitrogen.

After formation of the anthracycline glycoside-cardiolipin complex, the complex is encapsulated in liposomes. Encapsulation is undertaken by introducing the complex into a solution containing lipids which will produce liposomes. The liposomes are preferably positive liposomes. Positive liposomes can be formed from a solution containing phosphatidyl choline, cholesterol and stearyl amine. Neagative liposomes are formed from solutions containing phosphatidyl chlorine, cholesterol and phosphatidyl serine.

Liposome formation and encapsulation involves dispersing the complex of anthracycline glycoside and cardiolipin in said lipid containing solution. Dispersion is generally undertaken by employing a magnetic stirrer for approximately 20 minutes to form the dispersion and/or sonicating the liposomes. The encapsulated product is isolated by removing free anthracycline glycoside from it. Free anthracycline glycoside can be isolated from encapsulated product by extensive dialysis, for example, against 0.001 M phosphate buffer with 0.85% NaCl at a pH of 7.4 and at 4° C. over a period of 30 hours with at least three changes of buffer solutions.

The weight of lipids forming liposomes will vary depending on the exact conditions used to form them and thus will range from about two times to about six times, based on the weight of anthracycline glycoside content. As will be seen below, liposome encapsulated cardiolipin complex selectively reduce the uptake of the complexed drug into the cardiac tissue with a concomitant decrease in acute cardiotoxicity. The treatment-limiting toxicity of most of the anthracycline glycosides or analogues is the cumulative damage of cardiac tissue, which places a limit on the total dose of these drugs that can be administered. It appears that delivery of these drugs in liposome encapsulated cardiolipin complex is of great clinical significance in ameliorating this problem.

The invention will be illustrated and explained by specific embodiments in the drawings and the examples, which are described below.

BRIEF DESCRIPTION OF THE DRAWINGS

FIG. 1 is a graph [of concentration of drug in heart tissue vs. time (hours)] in which the change in concentration in cardiac tissue of free Andriamycin administration over time is compared to the concentration in cardiac tissue of Adriamycin containing compositions of the invention after administration, and also the concentration in cardiac tissue of Adriamycin encapsulated in liposomes without forming a cardiolipin complex.

FIG. 2 is an electron micrograph of cardiac tissue from DBA/2 mouse after administration of 15 mg/kg i.v. free Adriamycin, which exhibits loss and fragmentation of myofilaments with concomitant clearing of organelles and swelling of sarcoplasmic areas.

FIG. 3 is an electron micrograph of cardiac tissue from a DBA/2 mouse after administration of 15 mg/kg of Adriamycin complexed with cardiolipin and encapsulated in liposomes in accordance with the invention, which exhibits a substantially normal appearing myocardium with limited toxic damage, manifested as vacuolization seen in vasular associated tissues between adjacent myoctyes.

EXAMPLES

Example 1

Preparation of an Anthracycline Glycoside-Cardiolipin-Liposome Composition of the Invention To prepare an Adriamycin-cardiolipin-complex encapsulated in liposome composition, 11.6 μmole of Adriamycin in methanol solution is mixed with 5.9 μmole of cardiolipin in ethanol in a flask. The two solutions are then slowly evaporated to dryness under a stream of nitrogen.

Then to the flask containing the dried Adriamycin and cardiolipin film are sequentially added the following lipids solution, (1) phosphatidyl choline, 28.5 μmole, (2) cholesterol, 19.4 μmole, and (3) stearyl amine, 11.5 μmole. The flask contents are gently stirred and are dried under nitrogen forming a thin film around the sides of the flask. The dried film of cardiolipin complex and lipids is then admixed with 6 ml of 0.9% NaCl and allowed to hydrate for 30 minutes. The contents of the flask are then agitated with a magnetic stirring bar for 10 minutes to yield multilamellar liposomes which are then sonicated in a bath-type instrument (Heat System 100 W) for 90 minutes with a continuous temperature control (37° C.). At 10 minute intervals during sonication, the contents of the flask are flushed with a stream of nitrogen. After the completion of sonication, the non-encapsulated Adriamycin was separated from liposomal encapsulated cardiolipin complex by extensive dialysis against 0.9% NaCl at 4° C. for 30 hours, as discussed above.

The amount of Adriamycin captured under these conditions was determined by fluorescence after the completion of dialysis. The amount of Adriamycin-cardiolipin complex encapsulated in liposomes was 55% (6.38 μmole) of the total input dose.

The various lipids which were used were obtained as follows: Phosphatidyl choline (bovine), and phosphatidyl choline (egg), phosphatidyl serine (bovine) and cholesterol were obtained from Sigma Chemicals Corp. (St. Louis, Missiouri), and stearyl amine was obtained from K & K Laboratories (New York, New York). All lipids were used as obtained and were stored at −20° C. Adriamycin (MSC 123127) was supplied by the Developmental Therapeutic Branch, Division of Cancer Treatment, National Cancer Institute. All other chemicals were reagent grade.

EXAMPLE 2

Determination of Tissue Distribution of Adriamycin-Cardiolipin-Lipisomes Compositions after Administration The physiologic disposition of free Adriamycin and of liposome encapsulated Adriamycin cardiolipin complex was determined in DBA/2 mice weighing 20-25 gm. Mice were injected with free Adriamycin and Adriamycin-cardiolipin complex encapsulated in liposomes via the tail vein at a dose of 4 mg/kg and at 2% body weight. At sequential time points from 5 minutes to 24 hours after drug administration, mice were bled through orbital sinus in hepanized tubes. Plasma was separated immediately and stored at −20° C. Four mice in each treatment group were killed by cervical dislocation and heart, liver, kidney, spleen, lungs and small intestine were rapidly excised, rinsed in 0.9% NaCl and stored at −20° C. until assayed.

Plasama and tissues were analyzed by the fluorometric method of Bachur et al. described in *Cancer Chemother*. Rep. 54, 89-94 (1970). Briefly, plasma was extracted with 5 volumes of 0.3 N HCl–50% ethanol and tissues were homogenized with 20 volumes of the acid alcohol. Plasma and tissue homogenates were centrifuged at 15,000 rpm for 10 minutes and the clear supernatant was assayed fluorometrically in a Perkin Elmer equipment at 470 nm excitation and 585 nm emission. Control tissues obtained from mice treated with blank liposomes were read similarly in the fluorometer to correct for any endogenous fluorescence. Fresh Adriamycin standards were prepared in ) 0.3 N HCl—50% ethanol each day to calculate the concentration of Adriamycin in the tissue samples.

FIG. 1 represents the disposition of free Adriamycin and of Adriamycin cardiolipin complex encapsulated in liposomes in mice heart when administered i.v. in a single dose of 4 mg/kg. The peak drug concentration occurred in 30 minutes following free drug administration; the value being 8.3 μg/gm of acrdiac tissue. However, the peak drug cardiac uptake with Adriamycin cardiolipin complex encapsulated in liposomes occurred at 5 minutes, the drug equivalents being 3.4 μg/gm of cardia tissue which is only about 40% of the amount observed with free Adriamycin. By one hour the cardiac levels of Adriamycin cardiolipin complex encapsulated in liposomes were negligble when compared to equivalent free drug delivery. It appears that Adriamycin delivery in cardiolipin complex encapsulated in liposomes selectively retards the uptake of drug in cardiac tissue at all time points. Moreover, the total concentration of drug to which the cardiac tissue was exposed for the period of 24 hours was substantially reduced when Adriamycin was administered complexed with cardiolipin and encapsulated in liposomes. The tissue concentration x time (C×T) values for the 24 hour period of tissue concentration for the cardiac were 55.2 μg.hr.g$^{-1}$ with Adriamycin delivered in cardiolipin complex encapsulated in liposomes.

It is evident from FIG. 1 that cardiolipin complex encapsulated liposomes of Adriamycin retard the cardiac uptake of the drug more effectively than positive liposomes formed without cardiolipin. The C×T values for the 24 hour period for the positive liposomes is 40 μg.hr.g$^{-1}$ compared to only 4.2 μg.hr.g$^{-1}$ for cardiolipin complex-encapsulated liposomes.

To determine whether the reduced cardiac uptake of Adriamycin in cardiolipin complex encapsulated liposomes prevented cardiotoxicity, electron microscope studies of this organ were performed. DBA/2 mice were injected i.v. with free drug or drug entrapped in cardiolipin complex encapsulated liposomes at a dose of 15 mg/kg. Three mice in each group were sacrificed by cervical dislocation on day three, five and seven and hearts were immediately removed and placed in physiological saline. The apex of the left ventricle with part of the septum was dissected out and minced into one cubic mm blocks and fixed in 2.5% glutaraldehyde buffered with 0.1 M cacodylate, pH 7.2 for two hours at room temperature. The specimens were rinsed in buffer, osmicated in Bennett and Luft's collidin buffered osmium tetroxide, dehydrated in graded ethanols and acetone, and embedded in Epon. For electron microscopy, preliminary 1 μm Epon sections were stained with alkaline toluidine blue and appropriate areas were chosen for ultrathin sectioning, following which random sections were taken on 200 mesh copper grids and stained with uranyl acetate and lead citrate. A JEOL 100 S Electron microscope at an accelerating voltage of 80 KeV was utilized for viewing the sections.

FIG. 2 shows the extent and degree of toxic damage of myocardium of heart tissues from mice treated with free Adriamycin. In this toxic damage the individual myoctyes show degenerative changes with vacuolation of the smooth endoplasmic reticulum and loss of myofibrils. Progression of damage could be seen with greater intensity on day 7 after free Adriamycin administration to mice. However, mice treated with Adriamycin cardiolipin complex encapsulated in liposomes showed an overall appearance comparable to that of control tissue (FIG. 3). In general, the cardiolipin complex-encapsulated liposome group displayed a picture consistent with protection from the drug in those areas examined, i.e. major portions of the tissue appeared normal and there was only minor loss of parallel fibrillar arrangement and myofilaments in limited focal areas. As shown in FIG. 3, normal vasculature and intercalation of myoctyes is evident in cardiolipin complex-encapsulated liposomes. (Note: Clearance of occurrence adjacent to vasculature ×4000).

EXAMPLE 3

Determination of Antitumor Activity of Compositions of the Invention

To determine whether encapsulation of Adriamycin cardiolipin complex into liposomes reduced the antitumor activity of the drug, the effectiveness of liposomes-encapsulated Adriamycin cardiolipin complex against the murine P388 ascitic leukemia in DBA/2 mice was studied. Mice were injected i.p with 1×10$^5$ cells of P388 leukemia. Twenty-four hours after tumor implantation, mice were administered intraperitoneally free Adriamycin or cardiolipin complex-encapsulated liposome at a dose of 4 mg/kg. Control mice received 0.9% NaCl or blank liposomes representing the same concentration of lipids as used to encapsulate Adriamycin cardiolipin complex. All injections were made on 2% body weight basis. Mice were weighed on day of injection, doses of drugs were calculated on body weight basis, and the survival time of mice was recorded in days.

Table 1 shows the effectiveness of free Adriamycin and cardiolipin complex-encapsulated liposomes on the survival of mice bearing P388 tumor. Mice when injected with free Adriamycin at a dose of 4 mg/kg i.p. exhibited a T/C of 132% (Treated vs. Control). The same dose of Adriamycin when injected as the cardiolipin complex-encapsulated liposome composition of the invention produced a survival rate of 125% T/C. These studies clearly demonstrate that there is no loss of antitumor activity of Adriamycin when it is complexed with cardiolipin and encapsulated in liposomes.

TABLE 1

Effect of Free and Cardiolipin Complex-Encapsulated Liposome Adriamycin on Survival of DBA/2 Mice Bearing P388 Tumor

| | | T/C (%) | |
|---|---|---|---|
| Route | Dose (mg/kg) | Free Adriamycin | Adriamycin in Cardiolipin Liposomes |
| i.p. | 4 | 132 | 125 |

Mice weighing 20 to 25 g were given i.p. injections of 10$^5$ cells and 24 hours later free or cardiolipin complex-encapsulated liposome Adriamycin was administered.

The foregoing description of the invention has been directed to particular details of the invention for purposes of explanation and illustration. It will be apparent, however, to those skilled in this art that many modifications and variations may be made without departing from the scope and spirit of the invention and that the appended claims embrace all such equivalent modifications and variations as fall within the true scope and spirit of the invention.

What is claimed is:

1. A cardiolipin complexed anthracycline glycoside compound encapsulated in liposomes formed from phosphatidyl choline, cholesterol and stearyl amine wherein said anthracycline glycoside is selected from the group consisting of doxorubicin, daunorubicin and pharmaceutically acceptable derivatives or salts thereof.

2. The compound of claim 1 having reduced cardiac toxicity compared to uncomplexed compound.

3. A method of preparing a cardiolipin complexed anthracycline glycoside compound selected from the group consisting of doxorubicin, daunorubicin and pharmaceutically acceptable derivatives or salts thereof comprising:
   (i) admixing said anthracycline glycoside with an amount of cardiolipin sufficient to complex with said anthracycline glycoside ranging from about 30% to 70% based on the weight of the anthracycline glycoside, so that an anthracycline glycoside cardiolipin complex is formed;

(ii) dissolving said complex in a composition comprising a solution containing, in a molar ratio of about 2.5:1.7:1 based on the amount of glycoside, respectively of phosphatidyl choline, cholesterol and stearyl amine; (iii) drying the resulting mixture; (iv) dispersing said dried mixture in 0.9% NaCl solution for about 20 minutes to form liposomes encapsulating said complex; and (v) isolating the encapsulated complex.

4. The method of claim 3, wherein said isolating comprises dialyzing against 0.001 M phosphate buffer with 0.85% NaCl at a pH of about 7.4 at about 4° C. over a period of about 30 hours with at least three changes of buffer solution.

5. A method of reducing cardiac toxicity while maintaining the inherent antibiotic or oncolytic activity of an anthracycline glycoside selected from the group consisting of doxorubicin, daunorubicin and pharmaceutically acceptable analogue, derivative or salt thereof, to a host, which anthracycline glycoside is selectively taken up by cardiac tissue of the host, comprising delivering with a pharmaceutically acceptable carrier the encapsulated compound of claim 1 to the host.

6. The compound of claim 1 wherein said liposomes are positive or negative.

7. The compound of claim 6 wherein said liposomes are positive.

8. The compound of claim 6 wherein said liposomes are negative.

9. The method of claim 3 wherein said liposomes are positive or negative.

10. The method of claim 3 wherein said liposomes are positive.

11. The method of claim 3 wherein said liposomes are negative.

12. A therapeutic composition for reducing cardiac toxicity while maintaining inherent antibiotic or oncolytic activity of an anthracycline glycoside comprising a cardiolipin complexed anthracycline glycoside compound encapsulated in liposomes and a pharmaceutically acceptable carrier, said anthracycline glycoside being selected from the group consisting of doxorubicin, daunorubicin and pharmaceutically acceptable analogue, derivative or salt thereof.

13. The therapeutic compound of claim 12 wherein said liposomes are positive or negative.

14. The therapeutic compound of claim 13 wherein said liposomes are positive.

15. The therapeutic compound of claim 13 wherein said liposomes are negative.

* * * * *